US008742187B2

(12) United States Patent
Taylor et al.

(10) Patent No.: US 8,742,187 B2
(45) Date of Patent: Jun. 3, 2014

(54) VARIATIONS ON PRINS-LIKE CHEMISTRY TO PRODUCE 2,5-DIMETHYLHEXADIENE FROM ISOBUTANOL

(75) Inventors: Thomas Jackson Taylor, Highlands Ranch, CO (US); Joshua D. Taylor, Evergreen, CO (US); Matthew W. Peters, Highlands Ranch, CO (US); David E. Henton, Midland, MI (US)

(73) Assignee: GEVO, Inc., Englewood, CO (US)

( * ) Notice: Subject to any disclaimer, the term of this patent is extended or adjusted under 35 U.S.C. 154(b) by 114 days.

(21) Appl. No.: 13/451,026

(22) Filed: Apr. 19, 2012

(65) Prior Publication Data

US 2012/0271082 A1    Oct. 25, 2012

Related U.S. Application Data

(60) Provisional application No. 61/477,017, filed on Apr. 19, 2011, provisional application No. 61/478,607, filed on Apr. 25, 2011.

(51) Int. Cl.
*C07C 5/393* (2006.01)
*C07C 1/20* (2006.01)

(52) U.S. Cl.
USPC ........... 585/322; 585/319; 585/408; 585/603; 568/437

(58) Field of Classification Search
USPC .............. 585/322, 319, 408, 603; 568/437
See application file for complete search history.

(56) References Cited

U.S. PATENT DOCUMENTS

| | | |
|---|---|---|
| 2,391,188 A | 12/1945 | Patterson |
| 2,391,646 A | 12/1945 | Schulze et al. |
| 2,529,061 A | 11/1950 | Vergnaud |
| 2,554,054 A | 5/1951 | Owen |
| 2,813,119 A | 11/1957 | Taves |
| 2,894,978 A | 7/1959 | Katzschmann |
| 2,945,900 A | 7/1960 | Alexander et al. |
| 2,982,795 A | 5/1961 | Owen |
| 2,984,644 A | 5/1961 | Wheat |
| 3,002,035 A | 9/1961 | Hieronymus |
| 3,154,593 A | 10/1964 | Long |
| 3,301,906 A | 1/1967 | Besozzi et al. |
| 3,344,037 A | 9/1967 | Leavitt |
| 3,356,754 A | 12/1967 | Wofford |
| 3,445,521 A | 5/1969 | Callahan et al. |
| 3,509,237 A | 4/1970 | Aubrey |
| 3,513,193 A | 5/1970 | Katzschmann |
| 3,644,550 A | 2/1972 | Beuther et al. |
| 3,662,016 A | 5/1972 | Furuoya et al. |
| 3,686,341 A | 8/1972 | Eberly |
| 3,755,458 A | 8/1973 | Vrbaski et al. |
| 3,825,502 A | 7/1974 | Takenaka et al. |
| 3,827,968 A | 8/1974 | Givens et al. |
| 3,830,866 A | 8/1974 | D'Alessandro et al. |
| 3,832,418 A | 8/1974 | Bercik et al. |
| 3,836,603 A | 9/1974 | Connor, Jr. et al. |
| 3,850,981 A | 11/1974 | Trebellas et al. |
| 3,851,008 A | 11/1974 | Stowe et al. |
| 3,856,882 A | 12/1974 | Takagi et al. |
| 3,886,224 A | 5/1975 | Mitchell, Jr. |
| 3,887,612 A | 6/1975 | Shigeyasu et al. |
| 3,891,721 A | 6/1975 | Prudence |
| 3,959,400 A | 5/1976 | Lucki |
| 3,960,978 A | 6/1976 | Givens et al. |
| 3,997,621 A | 12/1976 | Brennan |
| 4,025,575 A | 5/1977 | Chang et al. |
| 4,096,340 A | 6/1978 | Fujii et al. |
| 4,100,220 A | 7/1978 | Bowman et al. |
| 4,112,011 A | 9/1978 | Kolombos |
| 4,129,600 A | 12/1978 | Childress et al. |
| 4,152,300 A | 5/1979 | Riesser |
| 4,190,608 A | 2/1980 | Grasselli et al. |
| 4,197,185 A | 4/1980 | Le Page et al. |
| 4,225,743 A | 9/1980 | Hoshiyama et al. |
| 4,229,320 A | 10/1980 | Slaugh |
| 4,229,603 A | 10/1980 | Lyon |
| 4,241,220 A | 12/1980 | Itaya et al. |
| 4,244,806 A | 1/1981 | Le Page et al. |
| 4,266,958 A | 5/1981 | Cummings |
| 4,293,722 A | 10/1981 | Ward et al. |
| 4,304,948 A | 12/1981 | Vora et al. |
| 4,324,646 A | 4/1982 | Le Page et al. |

(Continued)

FOREIGN PATENT DOCUMENTS

GB    1313083       4/1973
JP    10-237017 A   9/1998

(Continued)

OTHER PUBLICATIONS

"International Search Report," 4 pages, International Patent Appl. No. PCT/US 12/34225, United States Patent and Trademark Office (issued Oct. 12, 2012).

(Continued)

*Primary Examiner* — Thuan D Dang
(74) *Attorney, Agent, or Firm* — Cooley, LLP

(57) ABSTRACT

The method of the present invention provides a high yield pathway to 2,5-dimethylhexadiene from renewable isobutanol, which enables economic production of renewable p-xylene (and subsequently, terephthalic acid, a key monomer in the production of PET) from isobutanol. In addition, the present invention provides methods for producing 2,5-dimethylhexadiene from a variety of feed stocks that can act as "equivalents" of isobutylene and/or isobutyraldehyde including isobutanol, isobutylene oxide, and isobutyl ethers and acetals. Catalysts employed in the present methods that produce 2,5-dimethylhexadiene can also catalyze alcohol dehydration, alcohol oxidation, epoxide rearrangement, and ether and acetal cleavage.

17 Claims, 9 Drawing Sheets

(56) References Cited

U.S. PATENT DOCUMENTS

| | | |
|---|---|---|
| 4,329,493 A | 5/1982 | Hashizume et al. |
| 4,331,823 A | 5/1982 | Weider et al. |
| 4,342,876 A | 8/1982 | Klingman |
| 4,354,044 A | 10/1982 | Aoshima et al. |
| 4,385,157 A | 5/1983 | Auclair et al. |
| 4,393,259 A | 7/1983 | Ward et al. |
| 4,396,787 A | 8/1983 | Gluzek et al. |
| 4,398,920 A | 8/1983 | Guibet et al. |
| 4,423,267 A | 12/1983 | Dowling et al. |
| 4,448,643 A | 5/1984 | Lindner et al. |
| 4,456,779 A | 6/1984 | Owen et al. |
| 4,456,781 A | 6/1984 | Marsh et al. |
| 4,463,211 A | 7/1984 | Manning |
| 4,465,884 A | 8/1984 | Degnan et al. |
| 4,471,147 A | 9/1984 | Owen et al. |
| 4,499,316 A | 2/1985 | Garska et al. |
| 4,504,692 A | 3/1985 | Arakawa et al. |
| 4,504,693 A | 3/1985 | Tabak et al. |
| 4,518,796 A | 5/1985 | Aoshima et al. |
| 4,531,014 A | 7/1985 | Gregory et al. |
| 4,542,251 A | 9/1985 | Miller |
| 4,544,792 A | 10/1985 | Smith et al. |
| 4,612,406 A | 9/1986 | Long et al. |
| 4,621,164 A | 11/1986 | Chang et al. |
| 4,642,369 A | 2/1987 | Modic et al. |
| 4,663,406 A | 5/1987 | Bronstert et al. |
| 4,684,758 A | 8/1987 | Higashio et al. |
| 4,698,452 A | 10/1987 | Le Van Mao et al. |
| 4,720,600 A | 1/1988 | Beech, Jr. et al. |
| 4,720,601 A | 1/1988 | Suzukamo et al. |
| 4,740,652 A | 4/1988 | Frame |
| 4,788,376 A | 11/1988 | Mazurek et al. |
| 4,806,701 A | 2/1989 | Shum |
| 4,808,763 A | 2/1989 | Shum |
| 4,855,528 A | 8/1989 | Young et al. |
| 4,864,068 A | 9/1989 | Shamshoum |
| 4,873,392 A | 10/1989 | Le Van Mao |
| 4,908,471 A | 3/1990 | Leuck et al. |
| 4,950,828 A | 8/1990 | Shum |
| 4,975,402 A | 12/1990 | le van Mao et al. |
| 5,026,938 A | 6/1991 | Shum |
| 5,087,789 A | 2/1992 | McDaniel et al. |
| 5,107,050 A | 4/1992 | Gaffney et al. |
| 5,130,458 A | 7/1992 | Wu |
| 5,135,861 A | 8/1992 | Pavilon |
| 5,386,071 A | 1/1995 | Kuchar et al. |
| 5,414,160 A | 5/1995 | Sato et al. |
| 5,519,101 A | 5/1996 | Nubel et al. |
| 5,550,306 A | 8/1996 | Chauvin et al. |
| 5,625,109 A | 4/1997 | Gupta |
| 5,672,800 A | 9/1997 | Mathys et al. |
| 5,693,793 A | 12/1997 | Ritz et al. |
| 5,753,474 A | 5/1998 | Ramey |
| 5,801,286 A | 9/1998 | Besson et al. |
| 5,856,604 A | 1/1999 | Stine et al. |
| 5,877,372 A | 3/1999 | Evans et al. |
| 5,895,830 A | 4/1999 | Stine et al. |
| 5,962,604 A | 10/1999 | Rath |
| 5,969,178 A | 10/1999 | Okamoto et al. |
| 5,990,367 A | 11/1999 | Stine et al. |
| 5,994,601 A | 11/1999 | Nierlich et al. |
| 6,111,160 A | 8/2000 | Powers et al. |
| 6,143,942 A | 11/2000 | Verrelst et al. |
| 6,239,321 B1 | 5/2001 | Mossman et al. |
| 6,300,536 B1 | 10/2001 | Verrelst et al. |
| 6,323,384 B1 | 11/2001 | Powers et al. |
| 6,331,580 B1 | 12/2001 | Molnar |
| 6,358,717 B1 | 3/2002 | Blaschek et al. |
| 6,376,731 B1 | 4/2002 | Evans et al. |
| 6,600,081 B2 | 7/2003 | Manzer et al. |
| 6,649,757 B2 | 11/2003 | Kuroda et al. |
| 6,660,898 B1 | 12/2003 | Pyhälahti et al. |
| 6,689,927 B1 | 2/2004 | Frame et al. |
| 6,770,791 B2 | 8/2004 | Mathys et al. |
| 6,875,899 B2 | 4/2005 | Martens et al. |
| 6,884,916 B1 | 4/2005 | Brown et al. |
| 7,002,053 B2 | 2/2006 | Nierlich et al. |
| 7,012,167 B2 | 3/2006 | Kahn |
| 7,038,101 B2 | 5/2006 | Nurminen et al. |
| 7,067,708 B2 | 6/2006 | Manzer et al. |
| 7,161,053 B2 | 1/2007 | Beckmann et al. |
| 7,169,588 B2 | 1/2007 | Burch et al. |
| 7,183,450 B2 | 2/2007 | Brown et al. |
| 7,238,844 B2 | 7/2007 | Mathys et al. |
| 7,271,304 B2 | 9/2007 | Du Toit |
| 7,304,196 B2 | 12/2007 | Purola et al. |
| 7,329,788 B2 | 2/2008 | Tiitta et al. |
| 7,345,212 B2 | 3/2008 | Beadle et al. |
| 7,439,409 B1 | 10/2008 | Jan et al. |
| 7,498,473 B2 | 3/2009 | Zhou et al. |
| 7,553,997 B2 | 6/2009 | Stark et al. |
| 7,682,811 B2 | 3/2010 | Leschine et al. |
| 7,833,778 B2 | 11/2010 | Butler, III |
| 8,193,402 B2 | 6/2012 | Gruber et al. |
| 2002/0183578 A1 | 12/2002 | Commereuc et al. |
| 2003/0055179 A1 | 3/2003 | Ota et al. |
| 2004/0044261 A1 | 3/2004 | Feng et al. |
| 2005/0069998 A1 | 3/2005 | Ballesteros Perdices et al. |
| 2005/0112739 A1 | 5/2005 | Golubkov |
| 2005/0176870 A1 | 8/2005 | Kulkarni et al. |
| 2005/0183325 A1 | 8/2005 | Sutkowski |
| 2005/0228203 A1 | 10/2005 | Manzer |
| 2005/0228204 A1 | 10/2005 | Manzer |
| 2006/0111599 A1 | 5/2006 | Lamprecht et al. |
| 2007/0039239 A1 | 2/2007 | Forester et al. |
| 2007/0092957 A1 | 4/2007 | Donaldson et al. |
| 2007/0135665 A1 | 6/2007 | Wiese et al. |
| 2007/0148751 A1 | 6/2007 | Griffin et al. |
| 2007/0191662 A1 | 8/2007 | Oikarinen et al. |
| 2007/0202062 A1 | 8/2007 | Workman et al. |
| 2007/0215519 A1 | 9/2007 | Dierickx |
| 2007/0259410 A1 | 11/2007 | Donaldson et al. |
| 2007/0259411 A1 | 11/2007 | Bramucci et al. |
| 2007/0264697 A1 | 11/2007 | Taguchi et al. |
| 2007/0292927 A1 | 12/2007 | Donaldson et al. |
| 2008/0009656 A1 | 1/2008 | D'Amore et al. |
| 2008/0015395 A1 | 1/2008 | D'Amore et al. |
| 2008/0015397 A1 | 1/2008 | D'Amore et al. |
| 2008/0045754 A1 | 2/2008 | D'Amore et al. |
| 2008/0057555 A1 | 3/2008 | Nguyen |
| 2008/0124774 A1 | 5/2008 | Bramucci et al. |
| 2008/0131948 A1 | 6/2008 | Manzer et al. |
| 2008/0132730 A1 | 6/2008 | Manzer et al. |
| 2008/0132732 A1 | 6/2008 | Manzer et al. |
| 2008/0132741 A1 | 6/2008 | D'Amore et al. |
| 2008/0138870 A1 | 6/2008 | Bramucci et al. |
| 2008/0182308 A1 | 7/2008 | Donaldson et al. |
| 2008/0183020 A1 | 7/2008 | Carter |
| 2008/0220488 A1 | 9/2008 | D'Amore et al. |
| 2008/0227940 A1 | 9/2008 | Wilson et al. |
| 2008/0234523 A1 | 9/2008 | Manzer et al. |
| 2008/0248540 A1 | 10/2008 | Yang |
| 2008/0261230 A1 | 10/2008 | Liao et al. |
| 2008/0274525 A1 | 11/2008 | Bramucci et al. |
| 2008/0312482 A1 | 12/2008 | Jan et al. |
| 2008/0312485 A1 | 12/2008 | Takai et al. |
| 2009/0030239 A1 | 1/2009 | D'Amore et al. |
| 2009/0061492 A1 | 3/2009 | Benning et al. |
| 2009/0068714 A1 | 3/2009 | Leschine et al. |
| 2009/0099401 A1 | 4/2009 | D'Amore et al. |
| 2009/0155869 A1 | 6/2009 | Buelter et al. |
| 2009/0171129 A1 | 7/2009 | Evanko et al. |
| 2009/0182163 A1 | 7/2009 | Foo et al. |
| 2009/0215137 A1 | 8/2009 | Hawkins et al. |
| 2009/0226990 A1 | 9/2009 | Hawkins et al. |
| 2009/0226991 A1 | 9/2009 | Feldman et al. |
| 2009/0239009 A1 | 9/2009 | Tanaka |
| 2009/0240068 A1 | 9/2009 | Rajendran |
| 2009/0247799 A1 | 10/2009 | Myllyoja et al. |
| 2009/0299109 A1 | 12/2009 | Gruber et al. |
| 2010/0108568 A1 | 5/2010 | De Klerk |
| 2010/0137647 A1 | 6/2010 | Bradin |
| 2010/0216958 A1 | 8/2010 | Peters et al. |
| 2011/0087000 A1 | 4/2011 | Peters et al. |

(56) References Cited

U.S. PATENT DOCUMENTS

| | | |
|---|---|---|
| 2011/0172475 A1 | 7/2011 | Peters et al. |
| 2011/0288311 A1 | 11/2011 | Frost et al. |
| 2011/0288352 A1 | 11/2011 | Peters et al. |
| 2012/0171741 A1 | 7/2012 | Peters et al. |
| 2012/0238787 A1 | 9/2012 | Gruber et al. |

FOREIGN PATENT DOCUMENTS

| | | |
|---|---|---|
| JP | 2001-2600 A | 1/2001 |
| JP | 2006-306731 A | 11/2006 |
| JP | 2007-61763 A | 3/2007 |
| WO | WO 03/053570 A1 | 7/2003 |
| WO | WO 03/070671 A1 | 8/2003 |
| WO | WO 2005/065393 A2 | 7/2005 |
| WO | WO 2005/073172 A1 | 8/2005 |
| WO | WO 2005/092821 A1 | 10/2005 |
| WO | WO 2007/091862 A1 | 8/2007 |
| WO | WO 2008/058664 A1 | 5/2008 |
| WO | WO 2008/113492 A1 | 9/2008 |
| WO | WO 2009/038965 A1 | 3/2009 |
| WO | WO 2009/039000 A2 | 3/2009 |
| WO | WO 2009/039333 A1 | 3/2009 |
| WO | WO 2009/039335 A1 | 3/2009 |
| WO | WO 2009/039347 A1 | 3/2009 |

OTHER PUBLICATIONS

"Written Opinion of the International Searching Authority," 8 pages, International Patent Appl. No. PCT/US 12/34225, United States Patent and Trademark Office (issued Oct. 12, 2012).
"International Preliminary Report on Patentability," 10 pages, International Patent Appl. No. PCT/US2010/025234, United States Patent and Trademark Office (issued Aug. 30, 2011).
"International Search Report," 2 pages, from International Appl. No. PCT/US2010/051641, United States Patent and Trademark Office, Alexandria, Virginia, USA (mailed Dec. 2, 2010).
"International Search Report," 2 pages, from PCT appl. No. PCT/US2011/020549, United States Patent and Trademark Office, Alexandria, Virginia, United States (mailed Mar. 11, 2011).
"International Search Report," 2 pages, International Patent Appl. No. PCT/US2011/058766, United States Patent and Trademark Office (Feb. 17, 2012).
"International Search Report," 2 pages, International Patent Appl. No. PCT/US2011/035769, United States Patent and Trademark Office (Aug. 17, 2011).
"International Search Report," 4 pages, International Patent Application No. PCT/US2008/085423, United States Patent and Trademark Office, Alexandria, Virginia, United States (mailed Jul. 15, 2009).
"International Search Report," 5 pages, International Patent Appl. No. PCT/US2010/025234, United States Patent and Trademark Office (mailed Jun. 15, 2010).
"Part 2, Oxidative Dehydrodimerization of Alkenes", Catalysis Today, (1992), 343-393.
"Written Opinion of the International Searching Authority," 5 pages, International Patent Appl. No. PCT/US2011/058766, United States Patent and Trademark Office (Feb. 17, 2012).
"Written Opinion of the International Searching Authority," 5 pages, International Patent Appl. No. PCT/US2011/035769, United States Patent and Trademark Office (Aug. 17, 2011).
"Written Opinion of the International Searching Authority," 6 pages, International Patent Application No. PCT/US2008/085423, United States Patent and Trademark Office, Alexandria, Virginia, United States (mailed Jul. 15, 2009).
"Written Opinion of the International Searching Authority," 7 pages, from International Appl. No. PCT/US10/51641, United States Patent and Trademark Office, Alexandria, Virginia, USA (mailed Dec. 2, 2010).
"Written Opinion of the International Searching Authority," 9 pages, International Patent Appl. No. PCT/US2010/025234, United States Patent and Trademark Office (mailed Jun. 15, 2010).

"Written Opinion of the International Searching Authority," 9 pages, from PCT appl. No. PCT/US11/20549, United States Patent and Trademark Office, Alexandria, Virginia, United States (mailed Mar. 11, 2011).
Amin et al., "Dealuminated ZSM-5 Zeolite Catalyst for Ethylene Oligomerization to Liquid Fuels", Journal of Natural Gas Chemistry 2002, 11, 79-86.
Angermayr et al., "Energy Biotechnology with Cyanobacteria" Current Opinion in Biotechnology Jun. 2009, vol. 20, pp. 257-263.
ASTM International, "Standard Specification for Automotive Spark-Ignition Engine Fuel," Designation D4814-11, 31 pages (Jul. 2011).
ASTM International, "Standard Specification for Aviation Gasolines," Designation D910-11, 8 pages (May 2011).
ASTM International, "Standard Specification for Aviation Turbine Fuels," Designation D1655-11a, 16 pages (Aug. 2011).
ASTM International, "Standard Specification for Diesel Fuel Oils," Designation D975-11, 25 pages (Apr. 2011).
ASTM test method D 6866-05, "Determining the Biobased Content of Natural Range Materials Using Radiocarbon and Isotope Ratio Mass Spectrometry Analysis" 14 pages, 2005.
Atsumi "Direct photosynthetic recycling of carbon dioxide to isobutyraldehyde" Nature Biotechnology, Nov. 15, 2009, vol. 27, pp. 1177-1182.
Atsumi et al., "Non-fermentative Pathways for Synthesis of Branched-Chain Higher Alcohols as Biofuels", Nature, 2008, 451, p. 86-89.
Atsumi et al., Online Supplementary Information of "Non-fermentative Pathways for Synthesis of Branched-Chain Higher Alcohols as Biofuels", Nature, 2008, pp. 1-8.
Batist et al. "The catalytic oxidation of 1-butene over bismuth molybdate catalysts: II. Dependence of activity and selectivity on the catalyst composition" Journal of Catalysis, Feb. 1966, vol. 5, pp. 55-64.
Bekker and Prinsloo, "Butene Oligomerization over Phosphoric Acid: Structural Characterization of Products," Ind. Eng. Chem. Res. 48(22):10156-10162 (2009).
Bezergianni et al., "Catalytic Hydrocracking of Fresh and Used Cooking Oil," Ind. Eng. Chem. Res. 48:8402-8406 (2009).
Busca, "Acid Catalysts in Industrial Hydrocarbon Chemistry" Chemical Reviews, 2007, 107, 5366-5410.
Buyanov et al. "Catalysts and Processes for Paraffin and Olefin Dehydrogenation," Kinetics and Catalysis, Jan. 2001, vol. 42, pp. 64-75.
Čejka et al., "Acid-Catalyzed Sythesis of Mono- and Dialkyl Benzenes over Zeolites: Active Sites, Zeolite Topology, and Reaction Mechanisms", Catalysis Review 2002, 44(3), 375-421.
Chen and Yan, "M2 Forming—A Process for Aromatization of Light Hydrocarbons", Ind. Eng. Chem. Process Des. Dev., 25 (1986), 151-155.
Connor et al. "Engineering of an *Escherichia coli* Strain for the Production of 3-Methyl-1-Butanol" Applied Envirionmental Microbiology, Sep. 2008, vol. 74, pp. 5769-5775.
de Klerk, "Can Fischer-Tropsch Syncrude Be Refined to On-Specification Diesel Fuel?" Energy Fuels 23:4593-4604 (2009).
de Klerk, "Distillate Production by Oligomerization of Fischer-Tropsch Olefins over Solid Phosphoric Acid," Energy Fuels 20:439-445 (2006).
de Klerk, "Fischer-Tropsch Refining," Title page and pp. i-xi, Ph.D. Thesis, University of Pretoria (Feb. 2008).
de Klerk, "Fischer-Tropsch refining: technology selection to match molecules," Green Chem. 10:1249-1279 (2008).
Delhomme et al. "Succinic acid from renewable resources as a C4 building-block chemical—a review of the catalytic possibilities in aqueous media" Green Chemistry, Jan. 2009, vol. 11(1), pp. 13-26.
Dexter et al. "Metabolic Engineering of Cyanobacteria for Ethanol Production" Energy & Environmental Science, Aug. 2009, vol. 2(8), pp. 857-864.
Dhaliwal et al. "Measurement of the Unsaturation of Butyl Rubbers by the Iodine Index Method" Rubber Chemistry and Technology, 1994, vol. 67, pp. 567-581.
Frame et al., "High Octane Gasoline from Field Butanes by the UOP Indirect Alkylation (InAlk) Process", Erdöl, Erdgas Kohle, 114(7-8) (1998), 385-387.

(56) References Cited

OTHER PUBLICATIONS

Genomatica, Inc. press release, 10 pages (2008/2009).
Gnep et al., "Conversion of Light Alkanes to Aromatic Hydrocarbons; II. Role of Gallium Species in Propane Transformation on GaHZSM5 Catalysts", Applied Catalysis 1988, 43, 155-166.
Guisnet et al., "Aromatization of short chain alkanes on zeolite catalysts," Appl. Catal. A, 1992, 89, p. 1-30.
Hileman et al., "Near-Term Feasibility of Alternative Jet Fuels," 152 pages, Rand Corporation, 2009.
Hobbie et al., "Intramolecular, compound-specific, and bulk carbon isotope patterns in $C_3$ and $C_4$ plants: a review and synthesis," New Phytologist, 2004, 161, p. 371-385.
Jung et al. "Oxidative Dehydrogenation of $C_4$ Raffinate-3 to 1,3-Butadiene in a Dual-bed Reaction System Comprising $ZnFe_2O_4$ and $Co_9Fe_3Bi_1Mo_{12}O_{51}$ Catalysts: A Synergistic Effect of $ZnFe_2O_4$ and $Co_9Fe_3Bi_1Mo_{12}O_{51}$ Catalysts" Catalysis Letters, Jul. 2008 vol. 123, pp. 239-245.
Kamath "Process Analysis for Dimerization of Isobutene by Reactive Distillation" Industrial & Engineering Chemistry Research, Feb. 1, 2006, vol. 45, pp. 1575-1582.
Krishnan et al. "Oxidative Dehydrogenation of 1-Butene over Manganese Oxide Octahedral Molecular Sieves" Journal of Catalysis, Jun. 1999, vol. 184, pp. 305-315.
Lamprecht, "Fischer-Tropsch Fuel for Use by the U.S. Military as Battlefield-Use Fuel of the Future", Energy & Fuels 2007, 21, 1448-1453.
Latshaw "Dehydration of Isobutane to Isobutene in a Slurry Reactor" Department of Energy Topical Report, 84 pages, Feb. 1994.
Lopez Nieto et al. "Selective Oxidation of n-Butane and Butenes over Vanadium-Containing Catalysts" Journal of Catalysis, Jan. 2000, vol. 189, pp. 147-157.
Mazumder et al., "Oxidative Dehydrodimerization and Aromatization of Isobutene on $Bi_2O_3$-$SnO_2$ Catalysts", Applied Catalysis A: General, 245 (2003), 87-102.
McAvoy, "Notice of Allowability," 5 pages, U.S. Appl. No. 12/327,723 (mailed Mar. 9, 2012).
McAvoy, "Office Action Summary," 5 pages, U.S. Appl. No. 12/327,723 (mailed Jan. 4, 2012).
McAvoy, "Office Action Summary," 6 pages, U.S. Appl. No. 13/441,468 (mailed Aug. 16, 2012).
McAvoy, "Office Action Summary," 7 pages, U.S. Appl. No. 12/327,723 (mailed Jan. 11, 2011).
McAvoy, "Office Action Summary," 7 pages, U.S. Appl. No. 13/441,459 (mailed Jul. 20, 2012).
McAvoy, "Office Action Summary," 8 pages, U.S. Appl. No. 12/327,723 (mailed Apr. 8, 2011).
McAvoy, "Supplemental Notice of Allowability," 4 pages, U.S. Appl. No. 12/327,723 (mailed Apr. 27, 2012).
Pines and Haag, "Alumina: Catalyst and Support. IX. The Alumina Catalyzed Dehydration of Alcohols," J. Am. Chem. Soc. 83:2847-2852 (1961).
Rossberg et al., "Chlorinated Hydrocarbons," in Ullmann's Encyclopedia of Industrial Chemistry 2002, Wiley VCH, published online Jul. 15, 2006.
Rumizen, "ASTM Aviation Synthetic Fuel Specification," $3^{rd}$ International Conference on Biofuel Standards, World Biofuels Markets Congress, 19 pages (Mar. 2010).
Saad et al., "Characterization of various zinc oxide catalysts and their activity in the dehydration-dehydrogenation of isobutanol" Journal of the Serbian Chemical Society 2008, vol. 73(10), pp. 997-1009.
Sakuneka et al., "Synthetic Jet Fuel Production by Combined Propene Oligomerization and Aromatic Alkylation over Solid Phosphoric Acid", Ind. Eng. Chem. Res., 47 (2008), 1828-1834.
Savidge and Blair, "Intramolecular Carbon Isotopic Composition of Monosodium Glutamate: Biochemical Pathways and Product Source Identification," J. Agric. Food Chem. 2005, 53, p. 197-201.
Schmidt, "Fundamentals and systematics of the non-statistical distributions of isotopes in natural compounds," Naturwissenschaften 2003, 90, p. 537-552.
Solymosi et al., Aromatization of Isobutane and Isobutene Over $Mo_2C$/ZSM-5 Catalyst, Applied Catalysis A: General, 278 (2004), 111-121.
Speiser et al., "Catalytic Ethylene Dimerization and Oligomerization: Recent Developments with Nickel Complexes Containing P,N-Chelating Ligands", Accounts of Chemical Research 2005, 38, 784-793.
Subramani et al. "A Review of Recent Literature to Search for an Efficient Catalytic Process for the Conversion of Syngas to Ethanol" Energy and Fuels, Jan. 31, 2008 vol. 22, pp. 814-839.
Suresh et al., "Engineering Aspects of Industrial Liquid-Phase Air Oxidation of Hydrocarbons", Ind. Eng. Chem. Res. 39 (2000), 3958-3997.
Syu, "Biological production of 2,3-butanediol" Applied Microbiology and Biotechnology, Jan. 2001, vol. 55(1), pp. 10-18.
Taubert et al., "Dehydrodimerization of Isobutene to 2,5-Dimethyl-1,5-hexadiene over Bismuth-(III)-Oxide and Various Additives", Chem. Eng. Technol., 29(4) (2006), 468-472.
Threadingham et al., "Rubber, 3. Synthetic," in Ullmann's Encyclopedia of Industrial Chemistry 2002, Wiley VCH, published online Apr. 30, 2004.
Tiwari et al. "Effect of aluminium oxide on the properties of Cu-Mo catalyst in the oxidative dehydrogenation of butene-1 to butadiene" Journal of Catalysis, Nov. 1989, vol. 120, pp. 278-281.
Toledo-Antonio et al. "Correlation between the magnetism of non-stoichiometric zinc ferrites and their catalytic activity for oxidative dehydrogenation of 1-butene" Applied Catalysis A: General, Aug. 2002, vol. 234, pp. 137-144.
UOP, "Cyclar™" (process fact-sheet).
UOP, UOP Indirect Alkylation (InAlk™) Process Mixed Olefins Application (process fact sheet).
Weber et al., "13C-Pattern of Natural Glycerol: Origin and Practical Importance," J. Agric. Food Chem. 1997, 45, p. 2042-2046.
Wyman, "Potential Synergies and Challenges in Refining Cellulosic Biomass to Fuels, Chemicals, and Power", 2003 Biotechnological Progress 19:254-62.

diisobutyl acetal of isobutyraldehyde

VARIATIONS ON PRINS-LIKE CHEMISTRY TO PRODUCE 2,5-DIMETHYLHEXADIENE FROM ISOBUTANOL

This application claims the benefit of U.S. Provisional Patent Application No. 61/477,017, filed Apr. 19, 2011, and U.S. Provisional Patent Application No. 61/478,607, filed Apr. 25, 2011, each of which is incorporated herein by reference in its entirety.

BACKGROUND

Aromatic compounds are conventionally produced from petroleum feedstocks in refineries by reacting mixtures of light hydrocarbons ($C_1$-$C_6$) and naphthas over various catalysts at high heat and pressure. The mixture of light hydrocarbons available to a refinery is diverse, and provides a mixture of aromatic compounds suitable for use in fuel once the carcinogenic benzene is removed. Alternatively, the hydrocarbon feedstocks can be purified into single components to produce a purer aromatic product. For example, aromatization of pure isooctene selectively forms p-xylene over some catalysts. The state of the art for production of 2,5-dimethyl-2,4-hexadiene (which can subsequently be dehydrocyclized to form p-xylene) typically uses isobutylene (obtained primarily from gas and oil crackers) and isobutyraldehyde (obtained by hydroformylation of propylene with syngas) as feed stocks (see FIG. 1).

Low molecular weight hydrocarbons can also be obtained by dehydration of low molecular weight alcohols produced via fermentation of biomass. For example, isobutanol can be dehydrated to provide isobutylene, a versatile 4 carbon synthon, which can then be dimerized under appropriate conditions to form 2,5-dimethylhexadiene.

However, conversion of low molecular weight alcohols (e.g., isobutanol) to 2,5-dimethylhexadiene may be difficult. For example, current methods for converting isobutylene (e.g., derived from isobutanol) to 2,5-dimethylhexadiene generally require high temperatures and oxygen co-feeds, which limit yields under typical conditions due to over oxidation of feedstock to carbon dioxide. Subsequent conversion of 2,5-dimethylhexadiene to p-xylene is typically a high yield, clean reaction over chromia (e.g., U.S. patent application Ser. No. 12/986,918, filed on Jan. 7, 2011, which is incorporated herein by reference in its entirety for all purposes) and other metal oxide catalysts. The reaction produces only p-xylene in the aromatic product and does so in high yield.

Further, using diisobutylene as a feedstock for the production of aromatic compounds (e.g., xylenes) generally results in some cracking (which affects yield) and the production of less desirable xylene isomers (e.g., o- and m-xylene) due to the presence of other and unavoidable isooctene isomers in the product stream from an isobutylene dimerization process.

The conversion of isobutylene and isobutyraldehyde over niobic oxide catalysts under acidic conditions to 2,5-dimethyl-2,4-hexadiene is known. Under similar conditions, t-butanol can be used in place of isobutylene since these conditions promote alcohol dehydration as well. For example, U.S. Pat. No. 4,684,758 employs catalysts which may include niobic acid to produce 2,5-dimethyl-2,4-hexadiene from blends ranging from 1-10:1 isobutylene/t-butanol to isobutyraldehyde. However, this process requires a discrete isobutyraldehyde feed for coupling with the isobutylene and/or t-butanol feed component(s). In addition, the isobutyraldehyde feed is conventionally prepared from other starting materials, such as propylene and formaldehyde, so the overall process entails multiple processing steps from multiple, different raw materials.

SUMMARY

The present disclosure provides various methods for producing isobutylene (or isobutylene equivalents) and isobutyraldehyde (or isobutyraldehyde equivalents) from isobutanol (which may be renewable isobutanol), either in separate reactions or in situ with an olefin-aldehyde condensation reaction to form 2,5-dimethylhexadiene and/or 2-methyl-2,4-heptadiene (see, e.g., FIG. 2). For example, isobutanol can be used as an isobutylene equivalent in the reaction and isobutylene oxide may be used as an isobutyraldehyde equivalent. These synthons can then be coupled to form the desired dienes, which can then be cyclized to form o- and p-xylene. State of the art conversion of isobutanol to p-xylene generally requires very high temperatures which may result in yield losses to coke and low value hydrocarbons due to feedstock cracking. In one embodiment, the present disclosure describes a route to p-xylene from isobutanol that minimizes yield losses and provides a higher overall yield than current state of the art. In some embodiments, the present methods may provide yields of p-xylene of at least 80%, at least 85%, at least 90%, at least 95% or greater.

The present invention advantageously provides for the direct use of isobutanol (including renewable isobutanol) as the sole input chemical. For example, a stream of isobutanol can be reacted under appropriate conditions to provide a product stream containing a desired fraction of isobutyraldehyde, e.g. via careful selection of oxidation catalysts and process conditions, and the partially oxidized product stream can then be reacted directly, eliminating the need for multiple feed stocks if so desired. Furthermore, the present invention provides for the conversion of isobutanol to isobutyraldehyde in the presence of water with slight modifications (e.g., excess water removal, acid catalysis, temperature, etc.). In addition, the presently described methods can produce para-xylene or ortho-xylene, amongst other products, as renewable high-value commodity chemicals in a final cyclization step.

The present invention includes a high yield pathway to 2,5-dimethylhexadiene from isobutanol. In some embodiments oxygen (or another inexpensive oxidant) may be employed, and because reaction temperatures are generally much milder, yield losses due to overoxidation are minimized. Accordingly, the relatively high yield enables economic production of renewable p-xylene (and subsequently, terephthalic acid, a key monomer in the production of PET) from biomass-derived isobutanol. Furthermore, the chemistry described herein is very flexible. For example, 2,5-dimethylhexadiene can be produced from a variety of feed stocks that can act as "equivalents" of isobutylene and/or isobutyraldehyde including isobutanol, isobutylene oxide, isobutyl isobutyrate, and isobutyl ethers and acetals, each of which may be derived from biomass-derived isobutanol.

Furthermore, certain catalysts described herein that can effect olefin-aldehyde coupling (or coupling of olefin and aldehyde equivalents) to produce 2,5-dimethylhexadiene can also catalyze alcohol dehydration, alcohol oxidation, esters to aldehydes and/or olefins, epoxide rearrangement, and ether and acetal cleavage (e.g., formation of coupling partners prior to a coupling reaction, or production of coupling partners in situ).

As described above, in conventional petrochemical refineries, isobutanol is typically obtained by reduction of isobutyraldehyde. However, there is no commercial process to reoxidize isobutanol back to isobutyraldehyde. Accordingly, any chemistry that favors starting with a more oxidized component—in this case, an aldehyde—typically starts with the aldehyde, not the alcohol. The chemistry and methods described herein use a single feedstock, isobutanol (which may be renewable), as a source of both isobutylene and isobutyraldehyde, and in certain cases both components may be produced in the same reactor.

These and other advantages will be described below with reference to the various embodiments.

DETAILED DESCRIPTION

Figure 1:
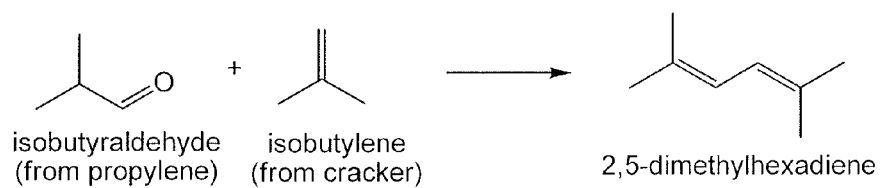
FIG. 1 shows a conventional aldehyde/olefin condensation reaction.
Figure 2:
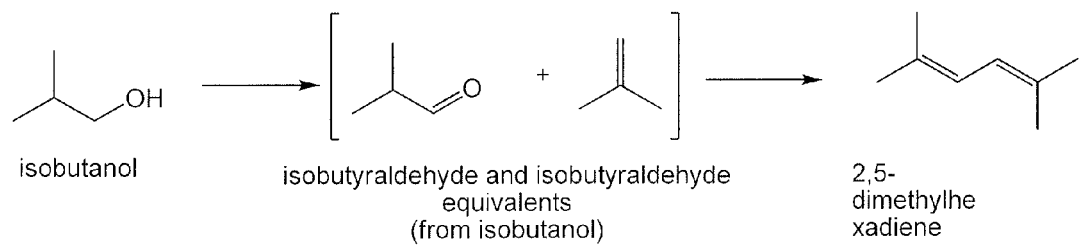
FIG. 2 shows an exemplary synthesis of 2,5,-dimethyl-2,4-hexadiene from isobutanol.

All documents cited herein are incorporated by reference in their entirety for all purposes to the same extent as if each individual document was specifically and individually indicated to be incorporated by reference.

"Renewably-based" or "renewable" as used herein denote that the carbon content of the renewable alcohol (and olefin, di-olefin, etc., or subsequent products prepared from renewable alcohols, olefins, di-olefins, etc. as described herein), is from a "new carbon" source as measured by ASTM test method D 6866-05, "Determining the Biobased Content of Natural Range Materials Using Radiocarbon and Isotope Ratio Mass Spectrometry Analysis", incorporated herein by reference in its entirety. This test method measures the $^{14}C/^{12}C$ isotope ratio in a sample and compares it to the $^{14}C/^{12}C$ isotope ratio in a standard 100% biobased material to give percent biobased content of the sample. "Biobased materials" are organic materials in which the carbon comes from recently (on a human time scale) fixated $CO_2$ present in the atmosphere using sunlight energy (photosynthesis). On land, this $CO_2$ is captured or fixated by plant life (e.g., agricultural crops or forestry materials). In the oceans, the $CO_2$ is captured or fixated by photosynthesizing bacteria or phytoplankton. For example, a biobased material has a $^{14}C/^{12}C$ isotope ratio greater than 0. Contrarily, a fossil-based material has a $^{14}C/^{12}C$ isotope ratio of about 0. The term "renewable" with regard to compounds such as alcohols or hydrocarbons (olefins, di-olefins, polymers, etc.) also refers to compounds prepared from biomass using thermochemical methods (e.g., Fischer-Tropsch catalysts), biocatalysts (e.g., fermentation), or other processes, for example as described herein.

A small amount of the carbon atoms of the carbon dioxide in the atmosphere is the radioactive isotope $^{14}C$. This $^{14}C$ carbon dioxide is created when atmospheric nitrogen is struck by a cosmic ray generated neutron, causing the nitrogen to lose a proton and form carbon of atomic mass 14 ($^{14}C$), which is then immediately oxidized to carbon dioxide. A small but measurable fraction of atmospheric carbon is present in the form of $^{14}CO_2$. Atmospheric carbon dioxide is processed by green plants to make organic molecules during the process known as photosynthesis. Virtually all forms of life on Earth depend on this green plant production of organic molecules to produce the chemical energy that facilitates growth and reproduction. Therefore, the $^{14}C$ that forms in the atmosphere eventually becomes part of all life forms and their biological products, enriching biomass and organisms which feed on biomass with $^{14}C$. In contrast, carbon from fossil fuels does not have the signature $^{12}C$ ratio of renewable organic molecules derived from atmospheric carbon dioxide. Furthermore, renewable organic molecules that biodegrade to $CO_2$ do not contribute to global warming as there is no net increase of carbon emitted to the atmosphere.

Assessment of the renewably based carbon content of a material can be performed through standard test methods, e.g. using radiocarbon and isotope ratio mass spectrometry analysis. ASTM International (formally known as the American Society for Testing and Materials) has established a standard method for assessing the biobased content of materials. The ASTM method is designated ASTM-D6866.

The application of ASTM-D6866 to derive "biobased content" is built on the same concepts as radiocarbon dating, but without use of the age equations. The analysis is performed by deriving a ratio of the amount of radiocarbon ($^{14}C$) in an unknown sample compared to that of a modern reference standard. This ratio is reported as a percentage with the units "pMC" (percent modern carbon). If the material being analyzed is a mixture of present day radiocarbon and fossil carbon (containing very low levels of radiocarbon), then the pMC value obtained correlates directly to the amount of biomass material present in the sample.

Throughout the present specification, reference to alcohols, olefins, di-olefins, etc., and higher molecular weight materials (e.g., isooctene/isooctane, polymers, copolymers, etc.) made from such compounds is synonymous with "renewable" alcohols, "renewable" olefins, "renewable" di-olefins, etc., and "renewable" materials (e.g., "renewable" isooctene/isooctane, "renewable" polymers, "renewable" copolymers, etc.) unless otherwise indicated. Unless otherwise specified, all such chemicals produced by the integrated processes described herein are renewable unless explicitly stated otherwise.

Throughout the present specification, the terms "olefin" and "alkene" are used interchangeably to refer to a hydrocarbon having at least one carbon-carbon double bond. Alkenes or olefins having two carbon-carbon double bonds can be referred to as dienes, and if the two carbon-carbon double bonds are adjacent in the molecule (e.g., four adjacent $sp^2$ carbon atoms), the molecule can be termed a conjugated diene.

The renewable alcohols, olefins, di-olefins, polymers, aliphatic and aromatic organic compounds, etc. of the present invention have pMC values of at least about 1, 5, 10, 15, 20, 25, 30, 35, 40, 45, 50, 55, 60, 65, 70, 75, 80, 85, 90, 95, 100, inclusive of all values and subranges therebetween.

Throughout the present specification, the term "about" may be used in conjunction with numerical values and/or ranges. The term "about" is understood to mean those values near to a recited value. For example, "about 40 [units]" may mean within ±25% of 40 (e.g., from 30 to 50), within ±20%, ±15%, ±10%, ±9%, 8%, ±7%, ±6%, ±5%, ±4%, ±3%, ±2%, ±1%, less than ±1%, or any other value or range of values therein or therebelow. Furthermore, the phrases "less than about [a value]" or "greater than about [a value]" should be understood in view of the definition of the term "about" provided herein.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

Throughout the present specification, the words "a" or "an" are understood to mean "one or more" unless explicitly stated otherwise. Further, the words "a" or "an" and the phrase "one or more" may be used interchangeably.

Figure 3:
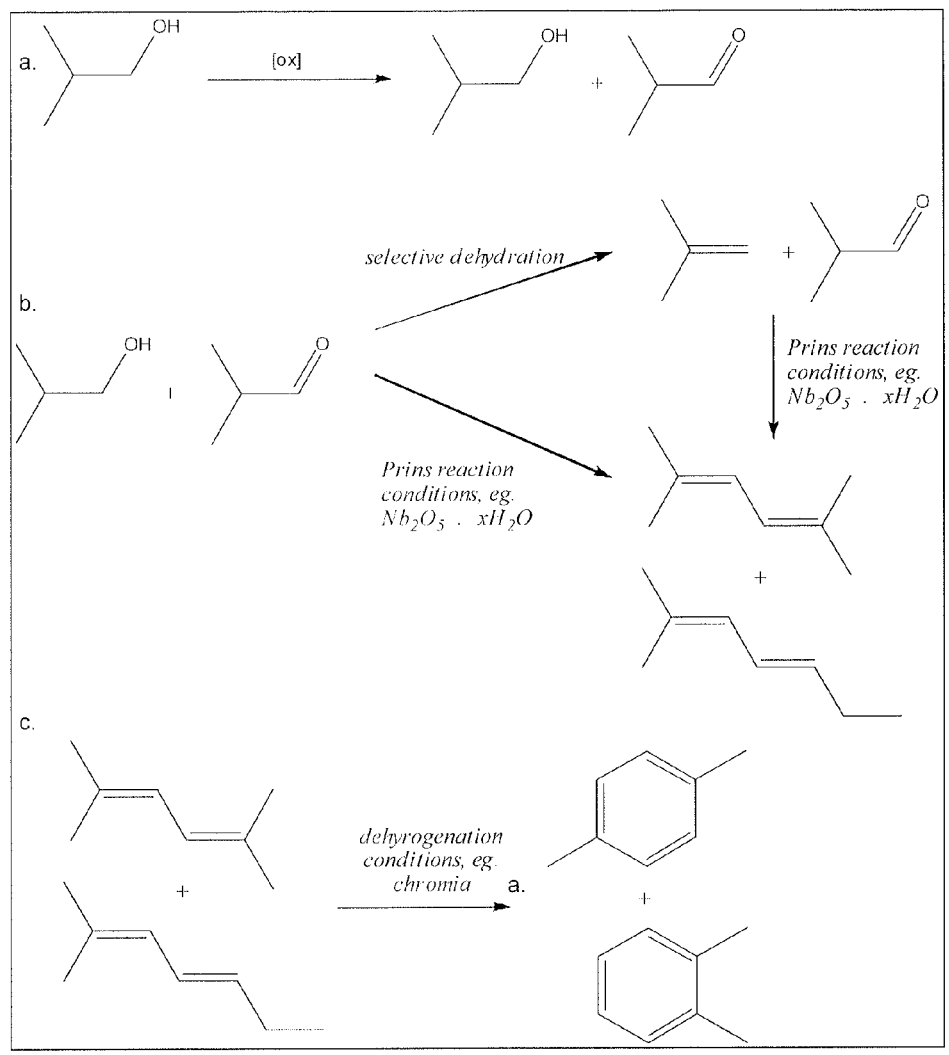
FIG. 3 shows exemplary routes for producing xylenes.

In one embodiment of the present invention, isobutanol, which may be renewable, can be partially oxidized or dehydrogenated by a suitable catalyst to isobutyraldehyde (see, e.g., FIG. 3a). Suitable oxidation catalysts, oxidants and methods to effect selective oxidation of isobutanol to isobutyraldehyde are known in the art. A product stream can thus be obtained having a specific ratio of isobutanol to isobutyraldehyde, as desired. For example, the ratio of isobutyraldehyde to isobutanol may range from 1:100 to 100:1, 1:10 to 10:1, 1:5 to 5:1, 1:4 to 4:1, 1:3 to 3:1, 1:2 to 2:1, 1:1 (or any other ratio or range of ratios therein). A particular ratio may be selected as described herein depending on a desired product and/or reaction conditions.

The partially oxidized mixture comprising isobutyraldehyde and isobutanol can be then passed over a dehydration catalyst to yield a mixture of isobutylene and isobutyraldehyde (see FIG. 3b). Typical dehydration catalysts that convert alcohols such as ethanol and isobutanol into ethylene and butene(s) include various acid treated and untreated alumina (e.g., γ-alumina) and silica catalysts and clays including zeolites (e.g., β-type zeolites, ZSM-5 or Y-type zeolites, fluoride-treated β-zeolite catalysts, fluoride-treated clay catalysts, etc.), sulfonic acid resins (e.g., sulfonated styrenic resins such as Amberlyst® 15), strong acids such as phosphoric acid and sulfuric acid, Lewis acids such boron trifluoride and aluminum trichloride, and many different types of metal salts including metal oxides (e.g., zirconium oxide or titanium dioxide) and metal chlorides (e.g., Latshaw B E, Dehydration of isobutanol to Isobutylene in a Slurry Reactor, Department of Energy Topical Report, February 1994).

The resultant mixture of isobutanol/isobutylene and isobutyraldehyde can be reacted over niobic acid (e.g., $Nb_xO_y \cdot nH_2O$), (either "as is," or primed with sulfuric or phosphoric acid or any other suitable mineral acid) on a support (which may include calcined transition or metalloid sulfates, or graphite, or any other suitable support) or a zeolite doped with a main-group or transition metal, or other suitable catalysts, at, e.g., 200-400° C. In the absence of excess water and acid, the reaction yields 2,5-dimethyl-2,4-hexadiene and/or 2-methyl-2,4-heptadiene (e.g., if 1-butene is present) with high selectivity. Excess isobutanol/isobutylene can be recycled to one of the previous steps when isobutyraldehyde is held as the limiting reagent. Alternatively, excess isobutyraldehyde can be removed and utilized as a renewable component in other chemical routes described herein (see FIG. 3b).

Figure 4:
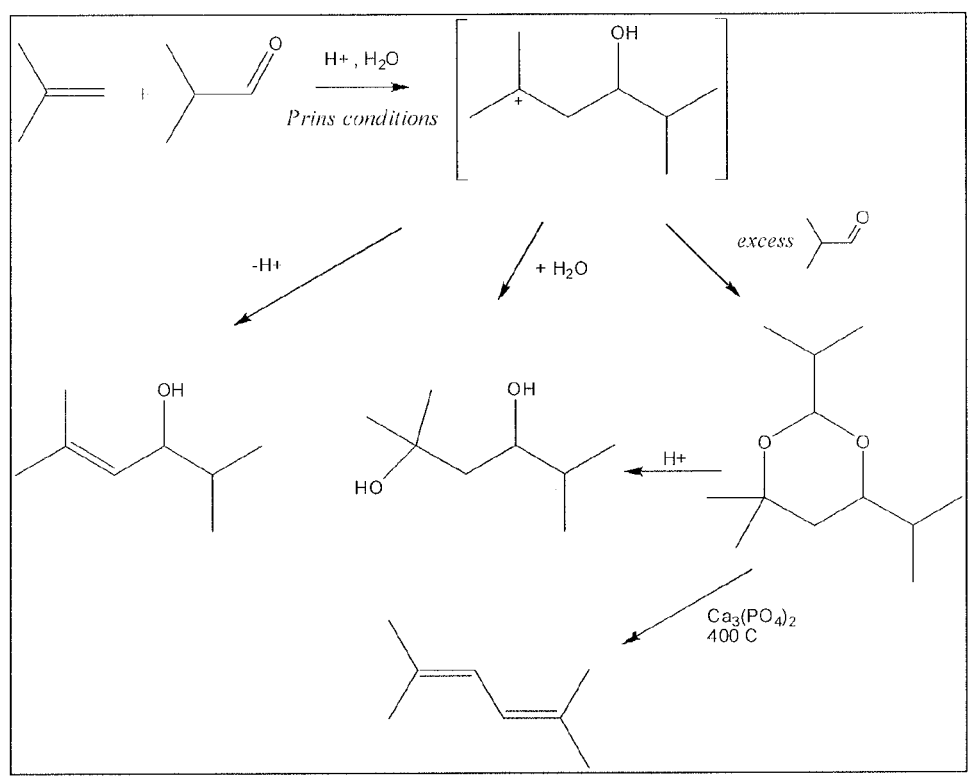
FIG. 4 shows exemplary routes for producing 2,5-dimethyl-2,4-hexadiene.

If coupling is performed in the presence of water and acid, more than 2 equivalents of isobutyraldehyde can be employed to favor acetal formation. The formed acetal can be further reacted over, e.g., calcium phosphate or another suitable catalyst to yield 2,5-dimethyl-2,4-hexadiene (see FIG. 4). It will be appreciated that more than one isomeric acetal may be possible. However, each isomeric acetal can be cleaved to form 2,5-dimethyl-2,4-hexadiene in a highly selective manner. Furthermore, reaction conditions can be selected to minimize formation of, or isomerization to, undesired products (e.g., by varying temperature, acid catalyst identity and amount, mole ratios of feed components and or water, reaction time, etc.). This is highly advantageous since subsequent cyclization of the preferred 2,5-dimethyl-2,4-hexadiene isomer can provide p-xylene in a highly selective manner.

In addition, while in certain embodiments, the present processes mat be employed to produce 2,5,-dimethyl-2,4-hexadiene, and subsequently convert 2,5,-dimethyl-2,4-hexadiene to p-xylene, other isomers may also be produced. For example, in some embodiments, the present methods may be employed to produce other isomers of dimethylhexadiene, including 2,4-dimethyl-2,4-hexadiene, which may be subsequently dehydrocyclized to form m-xylene, 2,3-dimethyl-2,4-hexadiene, which may be subsequently dehydrocyclized to form o-xylene.

In other embodiments, the present processes may be employed to form other dimethylhexadiene isomers, including 2,5,-dimethyl-1,4-hexadiene, 2,4,-dimethyl-1,4-hexadiene, and 2,3,-dimethyl-1,4-hexadiene, each of which may be dehydrocyclized to form the corresponding xylene isomer. Furthermore, dimethylhexenes may also be produced by the present methods (e.g., 2,5-dimethyl-1-hexene, 2,5-dimethyl-2-hexene, 2,5-dimethyl-3-hexene, 2,5-dimethyl-4-hexene, 2,5-dimethyl-5-hexene, 2,4-dimethyl-1-hexene, 2,4-dimethyl-2-hexene, 2,3-dimethyl-3-hexene, 2,4-dimethyl-4-hexene, 2,4-dimethyl-5-hexene; 2,3-dimethyl-1-hexene, 2,3-dimethyl-2-hexene, 2,3-dimethyl-3-hexene, 2,3-dimethyl-4-hexene, 2,3-dimethyl-5-hexene).

In other embodiments, dimethylhexanes may also be produced (e.g., 2,5-dimethylhexane, 2,4-dimethylhexane, 2,3-dimethylhexane). These saturated compounds may be used as a transportation fuel or fuel additive, e.g., gasoline or a gasoline blendstock. Partially unsaturated (e.g., dimethylhexenes) compounds produced as described herein may find utility as chemical building blocks, may be employed in further chemical transformations, or may be hydrogenated (e.g., dimethylhexenes) to produce a material suitable for use as a transportation fuel or fuel additive, e.g., gasoline or a gasoline blendstock.

Furthermore, the 2,5-dimethyl-2,4-hexadiene and/or 2-methyl-2,4-heptadiene produced via the methods described herein can then be reacted over a dehydrogenation catalyst, for example Houdry-type chromia catalyst at, e.g., about 350-550° C. to yield para-xylene and ortho-xylene, respectively, with high selectivity (see FIG. 3c).

Figure 5:
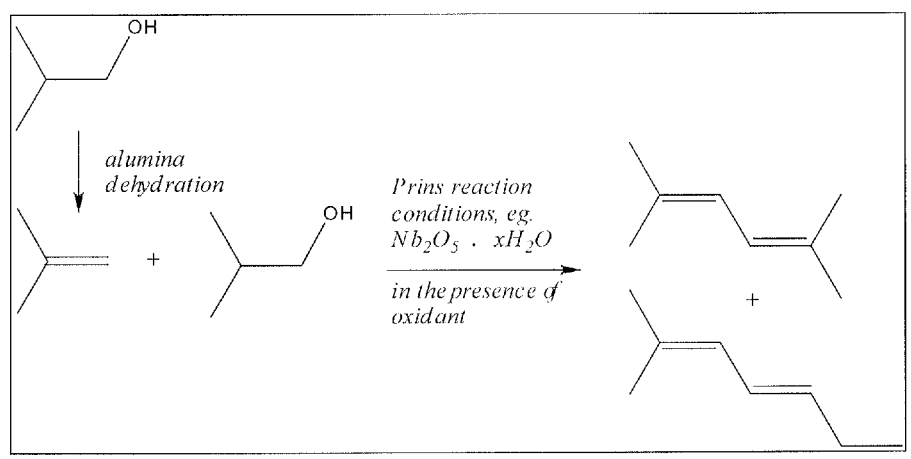
FIG. 5 shows exemplary routes for producing 2,5-dimethyl-2,4-hexadiene, 2-methyl-2,4-heptadiene and related alcohols.

In another embodiment, controlled oxidation of isobutanol (which may be renewable isobutanol) to isobutyraldehyde is provided by coupling said isobutyraldehyde (which may be produced as described herein from isobutanol) with isobutylene, without further oxidation to isobutyric acid. For example, isobutanol may be added directly over niobic acid (or any other suitable catalyst(s)) with an excess of isobutylene (which may be synthesized from isobutanol as described herein, and which may be renewable) in the presence of an oxidant (e.g., $O_2$, peroxides, etc.; see FIG. 5). As the isobutyraldehyde is formed it can directly react with excess isobutylene to yield the products mentioned above (e.g., 2,5-dimethyl-2,4-hexadiene and/or 2-methyl-2,4-heptadiene). Potential side products such as methacrolein (e.g., from oxidation of isobutylene), diisobutylene (e.g., from dimerization of isobutylene) are valuable chemicals in their own right, and may be recovered.

Figure 6:
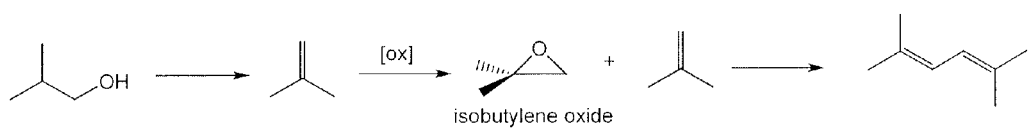
FIG. 6 shows an exemplary route for conversion of isobutanol to isobutylene and isobutylene oxide and production of 2,5-dimethyl-2,4-hexadiene therefrom.
Figure 7:
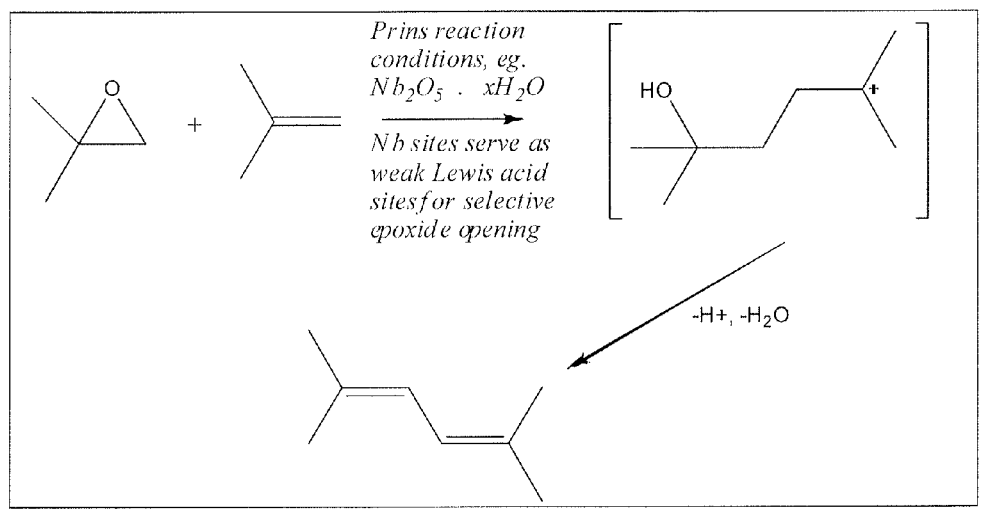
FIG. 7 shows an exemplary method for producing 2,5-dimethyl-2,4-hexadiene and 2-methyl-2,4-heptadiene.

In another embodiment, isobutylene oxide and isobutylene (both of which may be produced from isobutanol [which may be renewable] as described herein; see, e.g., FIG. 6) can be fed in tandem over niobic acid (or any other suitable catalyst(s)) and by regioselective epoxide ring-opening, the desired hexadiene backbone is created through dehydration, yielding 2,5-dimethyl-2,4-hexadiene (see FIG. 7). Alternatively, isobutanol may be directly fed over a niobic acid catalyst (or any other suitable catalyst(s)) in the presence of oxygen. Both isobutylene and isobutyraldehyde (or isobutylene oxide) may thus be formed in situ, and then converted to 2,5-dimethylhexadiene. It may also be possible to use isobutylene oxide (in the absence of an oxygen feed stream) as the sole feed stock for the reaction to produce a similar results (e.g., a similar product distribution with similar selectivity).

Renewable isobutylene oxide can be prepared by a variety of methods, including oxidation with cumene hydroperoxide (e.g., as described in EP 1382602 or U.S. Pat. No. 7,273,941) or oxidation with hydrogen peroxide. For example, isobutylene oxide may be derived from isobutylene by oxidation over a suitable catalyst typically with a "sacrificial" hydroperoxide reactant. Exemplary sacrificial catalysts may include cumene hydroperoxide (e.g., as described in EP 1382602 or U.S. Pat. No. 7,273,941) or tert-butyl hydroperoxide, which may provide valuable co-products after acting as an oxygen source for the formation of isobutylene oxide as described. Such valuable byproducts may be recovered. Alternatively, other oxidant may be employed (e.g., other peroxides) including hydrogen peroxide (e.g., in the presence of a titanium or vanadium silicalite catalyst as described in U.S. Pat. No. 7,273,941 or WO 97/47613). Other methods for oxidizing isobutylene to isobutylene oxide known in the art can also be used.

In another embodiment, isobutyl isobutyrate is used as an isobutyraldehyde equivalent since over metal oxide and Lewis acid catalysts, symmetrical esters are converted into two equivalents of corresponding aldehyde (e.g., U.S. Pat. No. 4,320,229). Isobutyl isobutyrate can be produced from isobutyraldehyde using Lewis acid catalysts, (e.g., the Tishchenko reaction), or isobutanol and isobutyric acid through conventional esterification chemistry. Isobutyl isobutyrate may be formed from isobutyraldehyde during the condensation of isobutyraldehyde with an isobutylene equivalent and may interconvert back to isobutyraldehyde in situ or removed and utilized as a renewable component in other chemical routes. Isobutyl isobutyrate may also act as an isobutylene equivalent since it may be converted into isobutylene and isobutyric acid over acidic catalysts or hydrolyzed to isobutanol and isobutyric acid.

Figure 8:
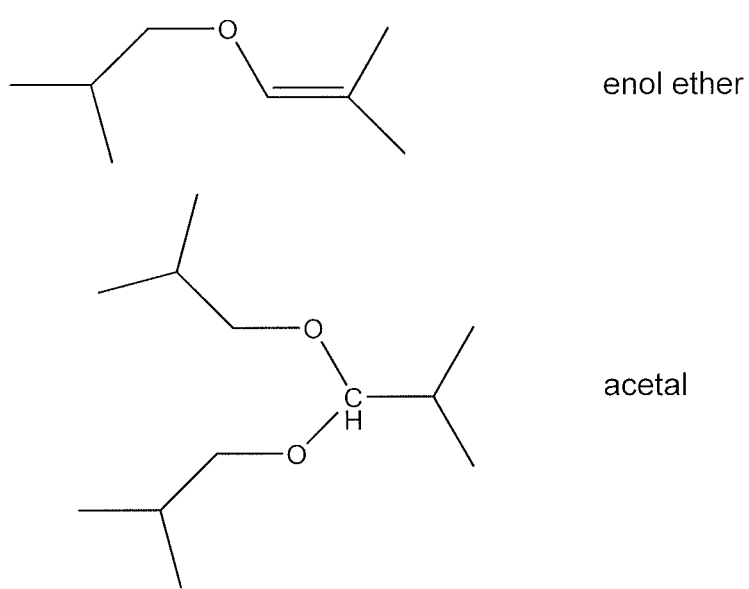
FIG. 8 shows exemplary isobutyraldehyde and isobutanol/isobutylene equivalents.

Another unique feature of the invention is that isobutanol can be treated to produce single molecule feed stocks for the condensation reaction that contain stoichiometric equivalents of isobutylene and isobutyraldehyde (e.g., enol ethers and acetals). Accordingly, in yet another embodiment, isobutanol and/or isobutene and isobutyraldehyde equivalents may be introduced to the reactor as a feedstock comprising a single compound. For example, if a one to one ratio of isobutanol/isobutene to isobutyraldehyde reactants is desired, the enol ether 1-(2-methyl-1-propoxy)-2-methylprop-1-ene can be the sole reactant in the reaction (see FIG. 8). Acid catalyzed cleavage of the enol ether to form isobutylene (or isobutanol, that may be dehydrated in situ to form isobutylene as described herein) and isobutyraldehyde can occur in a first reaction, then the isobutylene and isobutyraldehyde can be condensed to form 2,5-dimethylhexadiene (e.g., as described herein). If a two to one ratio of isobutanol/isobutene to isobutyraldehyde is desired, the diisobutyl acetal of isobutyraldehyde can be the sole reactant in the reaction (see FIG. 8).

Figure 9:
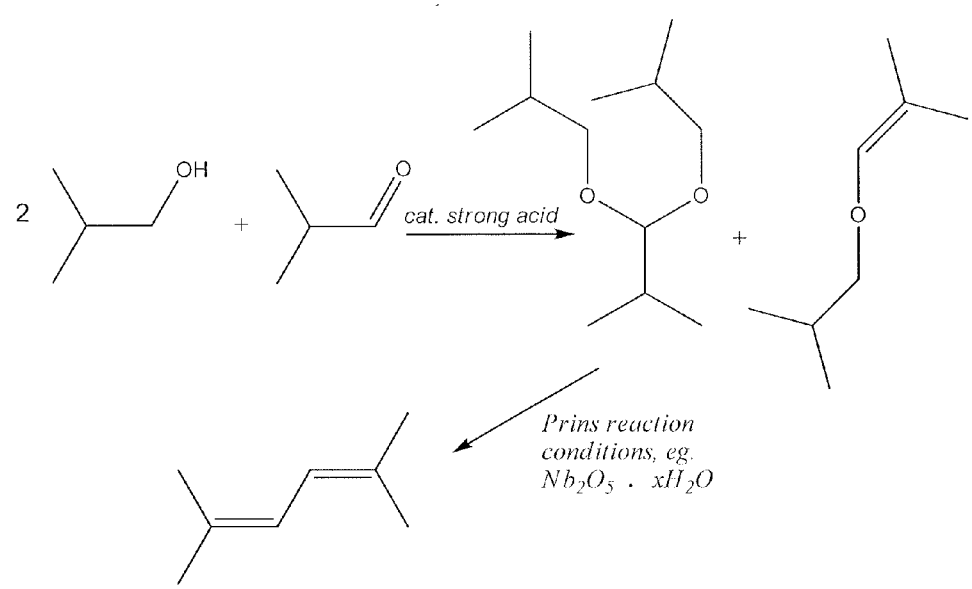
FIG. 9 shows an exemplary method of producing 2,5-dimethyl-2,4-hexadiene and 2-methyl-2,4-heptadiene.
Figure 10:
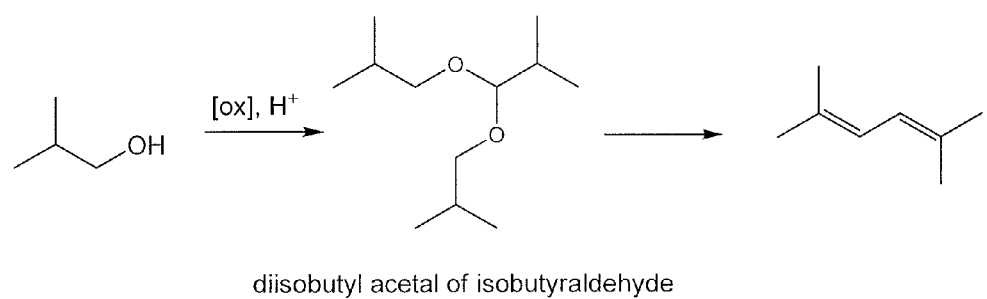
FIG. 10 shows an another exemplary method of producing 2,5-dimethyl-2,4-hexadiene.

As described for the enol ether decomposition reaction above, the acetal may be cleaved in situ to form two equivalents of isobutene (or isobutanol, which may be dehydrated in situ to isobutene) and one equivalent of isobutyraldehyde, which may then be condensed to form 2,5-dimethylhexadiene. Excess isobutylene can be recovered for further use (e.g., to form additional feedstock for ether synthesis). Both the enol ether and acetal described above may produced from isobutanol and isobutyraldehyde in the presence of acid catalysts, with a suitable mechanism or apparatus for removing water produced in the reaction (e.g., a Dean-Stark apparatus; see, e.g., FIG. 9), or may be produced from a single feed consisting solely of isobutanol (see, e.g., FIG. 10).

Niobic acid may be used as the catalyst in the above described processes because it is known to promote conversion of isobutylene and isobutyraldehyde to 2,5-dimethylhexadiene in high yields. However, the present methods are not so limited, and other metal oxide and/or acid catalyst may be employed to perform the reactions described herein. In one embodiment, the niobic acid may be mixed with metal sulfates. In another embodiment, the metal oxide catalyst has a composition with the general formula $X_aO_b$ wherein X is a metal or metalloid element and a and b are 0 to 6, with the proviso that a and b are not both 0 at the same time. In yet another embodiment the metal oxide catalyst contains multiple metal or metalloid elements and a corresponding amount of oxygen to balance the oxidation state of the metal/metalloid(s). In yet another embodiment, other non-metallic elements such halogens, sulfur, nitrogen, and phosphorus may replace oxygen in the metal/metalloid oxide compositions described above. Catalysts comprised of primarily silicon and/or aluminum oxides (e.g., zeolites, various alumina phases) as is or doped with metal or metalloid elements may also be used. Examples of catalysts that are known to catalyze the chemistry described herein include cation exchangers, metal halides, metal salts, phosphoric acid- and boric acid-derived materials, and 15% sulfuric acid. Further heterogeneous catalysts include tungsten oxide with and without supports (such as titania, silica, alumina, niobia, and zirconia), chromia with alumina support, silver-oxide with and without silica support, sulfur trioxide on zirconia ("Olefin-aldehyde condensation reaction on solid acids" Yamaguchi, T.; Nishimichi, C. *Cat. Today,* 1993, 16, 555-562.), pentasil-type catalysts with at least one metal/metalloid selected from boron, gallium, iron and aluminum, and the H-form of ZSM-5. The heterogeneous catalysts may be treated with concentrated or dilute acid solutions, often sulfuric or orthophosphoric acids.

If isobutanol is used as the sole feedstock, then oxygen is typically used as an oxidant when possible, but other inexpensive sacrificial oxidants such as hydrogen peroxide may also be used.

Advantageously, isobutanol is the sole feed stock for the various processes and methods described herein. Furthermore, the present processes which comprise more than one chemical transformation (e.g., conversion of isobutanol to isobutylene and to isobutyraldehyde) may be comprised of a single and unique reaction zone where several different chemical steps occur simultaneously. As discussed above, the acidic metal oxide catalysts described herein (e.g., niobic acid, etc.) can be used to catalyze multiple types of chemical reactions. For example, part of an isobutanol feed can be dehydrated to form isobutylene, while part of the same isobutanol feed stream can be oxidized to isobutyraldehyde, and then the isobutylene and isobutyraldehyde can be condensed to form, e.g., 2,5-dimethylhexadiene. Another example is the decomposition of the enol ether 1-(2-methyl-1-propoxy)-2-methylprop-1-ene to form isobutylene and isobutyraldehyde as described herein can occur in a first reaction, then the isobutylene and isobutyraldehyde can be condensed. Yet another example is the decomposition of the acetal discussed herein to form two equivalents of isobutylene and one of isobutyraldehyde as described herein can occur in a first reaction, then the isobutylene and isobutyraldehyde can be condensed.

The present methods may also be conducted in more than one reaction zone to form the condensation reactants. However, the first or upstream processes in a multi-reaction zone arrangement can be operated in a desired, specific way to produce the appropriate type and stoichiometry of feedstocks for a subsequent condensation reaction (e.g., to provide a desired ratio of isobutyraldehyde to isobutylene). For example, only a certain fraction of isobutanol may be oxidized to isobutyraldehyde to create a mixture of isobutanol and isobutyraldehyde that produces a desired product in a subsequent dehydration/condensation reaction.

The chemistry described herein may be performed neat with only the reactants being fed to the reactor or reactor zones. Alternatively, diluents may be used to aid in such functions such as controlling concentration, acting as a heat sink/carrier, moderating/eliminating unwanted side reactions, facilitating downstream processing, etc. Examples of diluents include inert gases or fluids such as nitrogen, argon, carbon dioxide, steam, methane, paraffins, acetonitrile, 1,4-dioxane, diethyl ether, tetrahydrofuran, etc. Typical temperatures for the reactions described above are between 100-400° C. These reactions can be performed in the gas, liquid, or supercritical phase at pressures between 1-100 atm. Typical weight hour space velocities are between 0.1-100 $hr^{-1}$. The reaction may be performed strictly in the absence of oxygen if oxidation of a feedstock is not a requirement of the reaction. Alternatively a reducing environment may favor desired product formation and minimize side product formation. In these cases a reducing diluent such as hydrogen or carbon monoxide may be used alone or in combination with other diluents.

In certain embodiments, the present reactions may be conducted at a pressures of from about 70 to about 570 psi; a temperature of from about 210 to about 315° C., and a WHSV of from about 1-10. In certain embodiments, the reaction is conducted with a feed comprising minimal diluents, e.g., less than about 25%, less than about 20%, less than about 15%, less than about 10%, less than about 5%, less than about 4%, less than about 3%, less than about 2%, or less than about 1% (by weight, by volume, or by mol %). In some embodiments, the oxygen content of the feed is minimized (e.g., less than about 5%, less than about 4%, less than about 3%, less than about 2%, less than about 1%, less than about 0.5%, less than about 0.1% [by weight, by volume, or by mol %]). In some embodiments, the water content of the feed minimized (e.g., less than about 5%, less than about 4%, less than about 3%, less than about 2%, less than about 1%, less than about 0.5%, less than about 0.1% [by weight, by volume, or by mol %]).

The present methods will be further illustrated by the following non-limiting examples:

EXAMPLES

Example 1

Dry renewable isobutanol is fed over a copper chromite catalyst (activated over nitrogen according to the manufacturer) at 320° C. and the WHSV of the addition slowed to the rate where the proportion of isobutyraldehyde required is achieved upon testing the effluent by GC/FID and $^1$H NMR. Proportions that would be potentially useful are 33% isobutyraldehyde/67% isobutanol, 50% isobutyraldehyde/50% isobutanol, 67% isobutyraldehyde/33% isobutanol, and above 99% isobutyraldehyde. During the reaction the material is tested often to monitor for excessive $CO_2$, propane, and/or isobutyric acid formation.

Example 2

The light phase azeotrope distilled from a mixture of water and renewable isobutanol is vaporized at 185° C. and diluted to 5% with helium. The stream is passed over a copper oxide catalyst on a particulate inert support. The oxidation proceeds stoichiometrically for 1 to 2 hours, then the reaction changes to endothermic as the CuO is exhausted and proceeds by anaerobic catalytic dehydrogenation over $Cu^0$, reaching a final temperature of 325° C. Renewable isobutyraldehyde is formed with 95% conversion and 98° A selectivity.

Example 3

One of the isobutanol/isobutyraldehyde mixtures from example 1 is passed over a mild dehydrogenation catalyst, selectively transforming the remaining isobutanol to isobutylene with 99% conversion and 96% selectivity, which may then be further used according to the methods taught in U.S. Pat. No. 4,684,758 where isobutylene and isobutyraldehyde are reacted over a niobic acid catalyst to produce 2,5-dimethylhexadiene in 90% yield.

Example 4

One of the isobutanol/isobutyraldehyde mixtures from example 1 is fed through a flow reactor charged with niobic acid catalyst at a rate of 40-60 g/hr at 225° C. Enough pressure (about 600 psi) is applied to keep the reactants in the liquid phase. The gas is collected as isobutylene and is directly recycled back into the reactor. The liquid effluent is sampled for conversion to 2,5-dimethyl-2,4-hexadiene, which is normally 35% with the remainder being unreacted starting material and a minor portion (5%) of higher isobutylene oligomers. At optimal conditions the reactor is continually run for periods longer than 10 days.

Example 5

One of the isobutanol/isobutyraldehyde mixtures from example 1, 1 part isobutyraldehyde to 2 parts isobutanol, is reacted in the presence of a catalytic amount of strong acid to form both the 1,1-diisobutoxy-3-methyl-butane (acetal) and the isobutyl isobutenyl ether (enol ether), in Dean-Stark conditions to drive the reaction to completion, proceeding at 95% conversion. These compounds are fed through a flow reactor charged with niobic acid catalyst at a rate of 40-60 g/hr at temperatures ranging from 200-300° C., most often 220° C. Enough pressure (50 psi) is applied to keep the reactants in the liquid phase. All gas is collected as isobutylene and is directly recycled back into the reactor. The liquid effluent is sampled for conversion to 2,5-dimethyl-2,4-hexadiene which is normally 35% with the remainder being unreacted starting material and a minor portion (5%) of higher isobutylene oligomers. At optimal conditions the reactor is continually run for periods longer than 10 days.

Example 6

Example 5 is repeated but at 600 psi with all the components in the supercritical phase. The conversion slightly lower, 30%, but the difference is made up in isobutyl isobutyrate which is recycled and gently treated so as not to form isobutyric acid upon disproportionation. The route taught by U.S. Pat. No. 4,320,229 is used to reform isobutyraldehyde from the ester in 90% conversion and recycled back to the reactor.

Example 7

Example 3 is repeated but in the presence of water, a catalytic amount of strong acid, and the mixture being in excess (2 equivalents to every equivalent isobutanol) of isobutyraldehyde. The secondary alcoholic carbocation formed in situ is trapped as an acetal by the excess isobutyraldehyde, specifically as 2,4-diisopropyl-6,6-dimethyl-1,3-dioxane, 80% conversion. The reaction mixture is fractionated either by distillation with any remaining isobutyraldehyde being re-used and the acetal removed with the bottoms. Alternatively the reaction is further driven to acetal creation (90%) by using Dean-Stark conditions. The collected acetal is introduced to a vessel charged with calcium phosphate, heated to 400° C., and cooled to yield 80% 2,5-dimethyl-2,4-hexadiene with some additional (5%) 2-methyl-2,4-heptadiene.

Example 8

A mixture of renewable isobutylene and isobutanol, made from partial dehydrogenating a batch of renewable isobutanol over alumina at 10 psi and 45 WHSV at 350° C., is fed through a flow reactor charged with niobic acid catalyst at a rate of 40-60 g/hr at temperatures ranging from 250-300° C., preferably 220° C. Enough pressure (about 600 psi) is applied to keep the reactants in the liquid phase. The liquid effluent is sampled for conversion to 2,5-dimethyl-2,4-hexadiene which is normally 35% with the remainder being unreacted starting material and a minor portion (5%) of higher isobutylene oligomers. At optimal conditions the reactor is continually run for periods longer than 10 days.

Example 9

Figure 12:
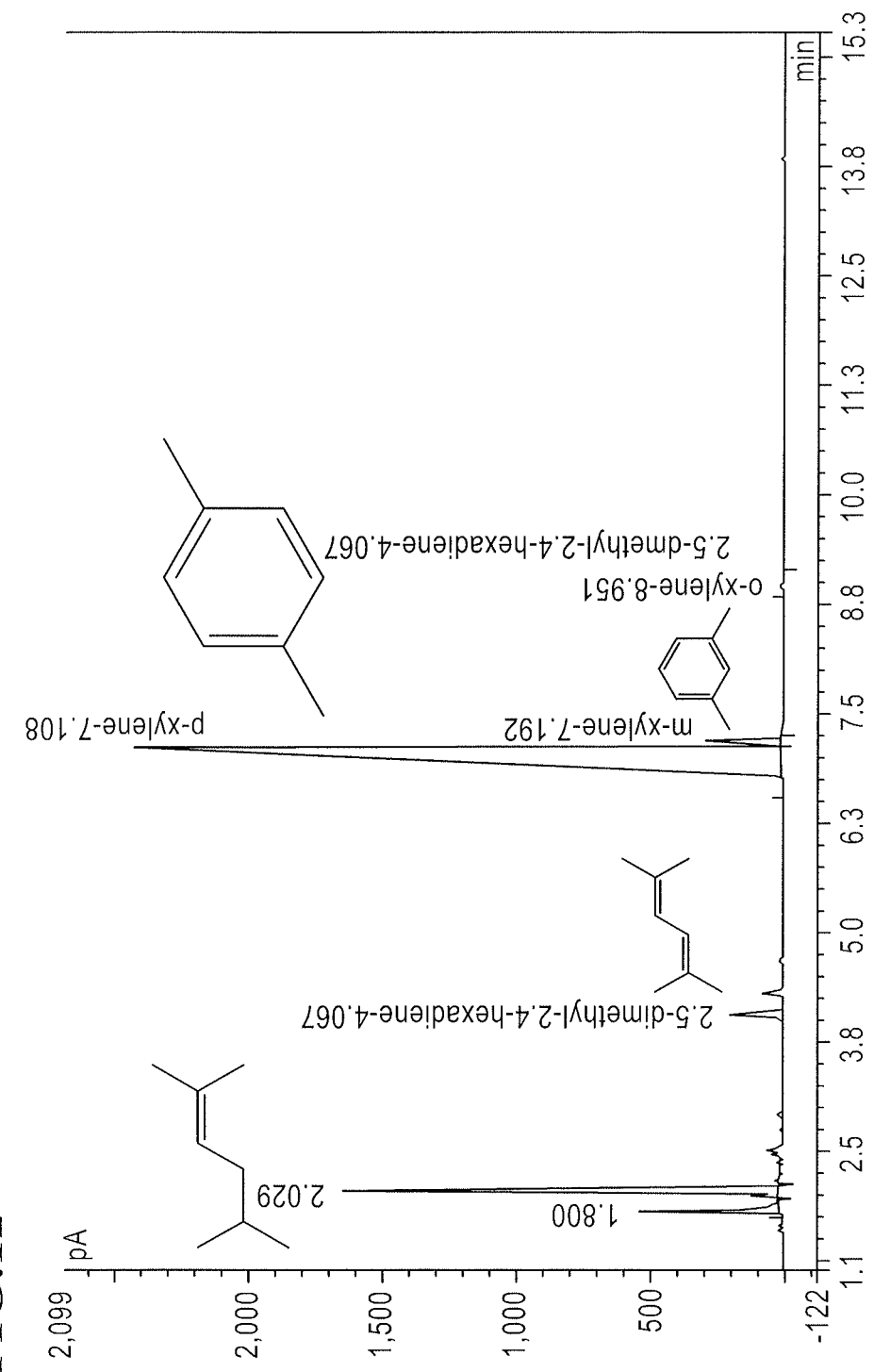
FIG. 12 shows the GC/FID trace of the effluent resulting from 2,5-dimethyl-2,4-hexadiene passed over chromia/alumina, with molecular structures of the compounds corresponding to the relevant peaks, as set out in Example 11.

Niobium oxide catalyst (Süd-Chemie, >5% graphite) was crushed to particles 1 to 2.8 mm in size, immersed in 0.1 N $H_3PO_4$ (aqueous) for 4 hours, washed 5 times in distilled water, then calcined at 350° C. overnight, similar to the catalyst preparation as taught by U.S. Pat. No. 4,684,758. The bottom of a stainless steel reactor with an inner diameter of ½" was filled with 4 mm borosilicate glass beads, then 15 g of the treated catalyst, and then filled with more beads. A solution of isobutyraldehyde and isobutanol (1:4 stoichiometry) was then flowed, 0.6 mL/min, through the reactor at 70-80 psi. Electrical tape was used to heat the reactor so that the material entering the catalyst region was about 215° C. and the product leaving the region was no more than 300° C. Ample butenes, primarily isobutylene, were produced. The organic phase was colored a deep yellow, and GC/FID indicated 33% of the material was 2,5-dimethyl-2,4-hexadiene, corresponding to a 25% yield. 95+% of the isobutyraldehyde was converted. See FIG. 12 for the GC/FID trace.

Example 10

2,5-dimethyl-2,4-hexadiene and, occasionally, 2-methyl-2,4-heptadiene collected from the reactions in examples 3-6 are separated by fractional distillation. Both of the isolated compounds are fed neat over alkaline-assisted chromia catalyst at 1 WHSV at 450° C. at ambient pressure. The feed is halted after 30 mins to yield liquid fractions with 82 and 80% of para and ortho-xylene, respectively, with an overall yield of 70% xylene from a single-pass. The remaining starting material, as well as partially hydrogenated C8s (e.g., 2,5-dimethyl-2-hexene), about 15% of the effluent, are promptly recycled back into the reactor after the respective xylene is removed by selective crystallization. At this point the original reactor is heated to 500° C. and exposed to air and regenerated for a period of 15 mins. Toluene is added during the feed to slow the deactivation of the catalyst, and this example can be applied to a battery of reactors running in tandem to allow continuous feed of the hydrocarbon while the deactivated reactors are regenerated.

Example 11

2,5-dimethyl-2,4-hexadiene (96%, Acros) was diluted to 50% with a nitrogen stream and then passed over a chromia/alumina catalyst (SNAP III, BASF) at a WHSV of a 0.89 $hr^{-1}$, at a variety of temperatures. The effluent was analyzed by GC/FID to determine the proportion of starting material, para-xylene product, as well as the small proportion of partially hydrogenated starting material, as summarized in the table below. The GC/FID trace for the 450° C. effluent is included as FIG. 11.

Figure 11:
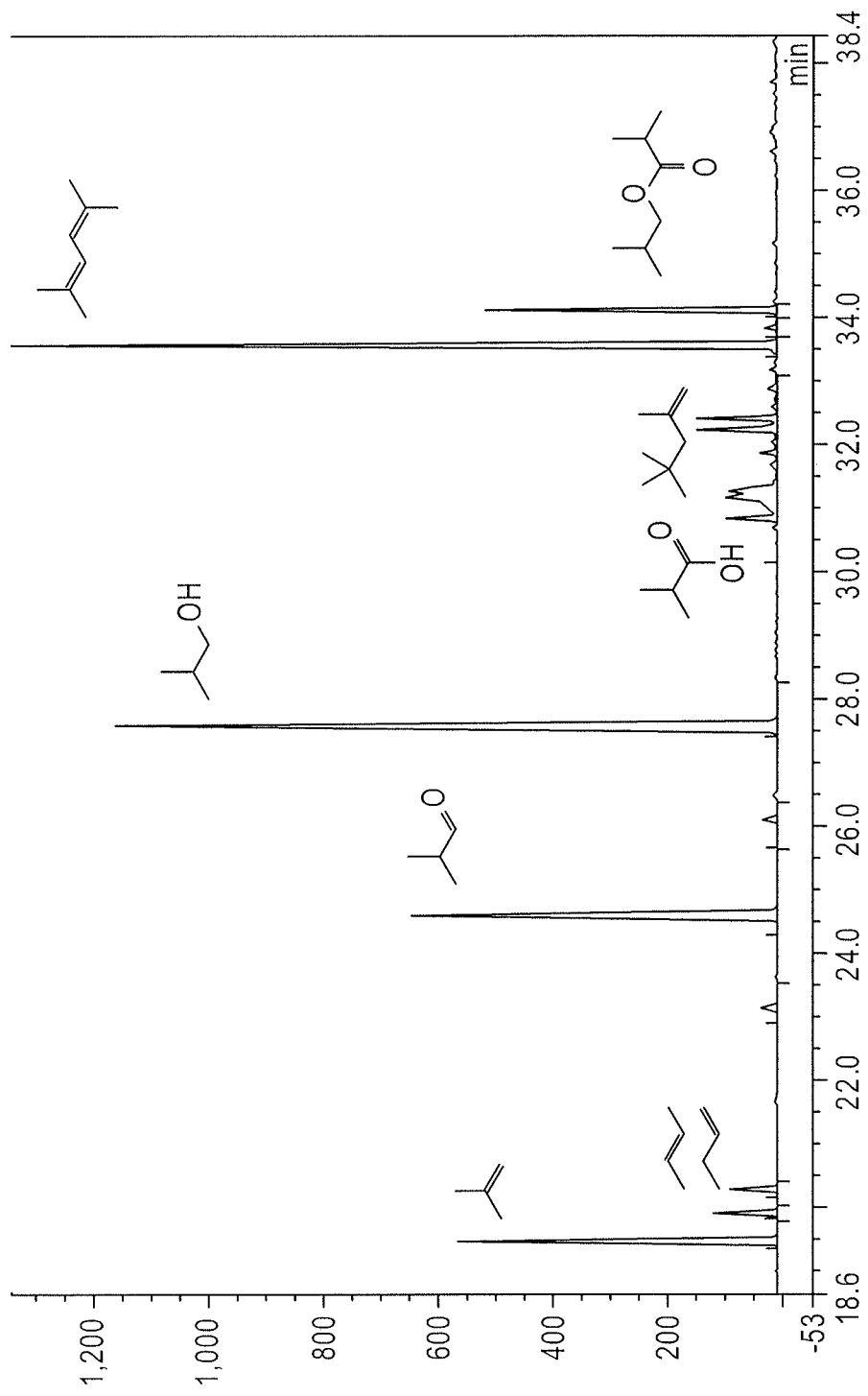
FIG. 11 shows the GC/FID trace of the effluent resulting from 4 parts isobutanol and 1 part isobutyraldehyde passed over niobic acid on graphite, with molecular structures of the compounds corresponding to the relevant peaks, as set out in Example 9.

| FIG. 11 | | | | | |
|---|---|---|---|---|---|
| Temperature (° C.) | DMH (%) | Various $C_8$ saturates (%) | Para-xylene (%) | Meta-xylene (%) | Ortho-xylene (%) |
| 250 | 91 | 9 | 1 | — | — |
| 300 | 78 | 16 | 4 | — | — |
| 350 | 49 | 33 | 19 | >1 | — |
| 400 | 10 | 33 | 55 | 1 | — |
| 450 | 2 | 13 | 82 | 2 | >1 |

Example 12

A stream of renewable isobutylene (95% from a dehydration reactor fed renewable isobutanol), is heated to 350° C. at 0.25 atm in the presence of 0.4 equivalents of ozone to produce a stream of 1 part isobutylene oxide and 2 parts isobutylene. The stream is partially cooled and fed through a flow reactor charged with niobic acid catalyst at a rate of 40-60 g/hr at 225° C. Enough pressure (600 psi) is applied to keep the reactants in the liquid phase. The excess gas collected is primarily isobutylene and is recycled back to mix with an enriched isobutylene oxide stream to ensure the 1:2 stoichiometry detailed above. The liquid effluent is sampled for conversion to 2,5-dimethyl-2,4-hexadiene, which is normally 65% with the remainder being unreacted starting material and a minor portion (5%) of higher isobutylene oligomers. At optimal conditions the reactor is continually run for periods longer than 10 days.

The embodiments described herein and illustrated by the foregoing examples should be understood to be illustrative of the present invention, and should not be construed as limiting. On the contrary, the present disclosure embraces alternatives and equivalents thereof, as embodied by the appended claims.

What is claimed is:

1. A method for preparing xylenes, comprising:
   a. providing a feedstock comprising isobutanol;
   b. at least partially oxidizing a portion of said isobutanol to form a first stream comprising isobutyraldehyde and isobutanol;
   c. coupling said isobutyraldehyde with isobutylene to form a second stream comprising 2,5-dimethyl-2,4-hexadiene; and
   d. dehydrocyclizing said 2,5-dimethyl-2,4-hexadiene to form a product stream comprising said xylenes.

2. The method of claim 1, wherein said isobutanol feedstock comprises renewable isobutanol.

3. The method of claim 2, wherein said isobutanol feedstock is renewable isobutanol.

4. The method of claim 1, wherein said isobutylene is formed via selective dehydration of said isobutanol in said first stream prior to said reacting step c.

5. The method of claim 1, wherein said xylenes comprise o-xylene and p-xylene.

6. The method of claim 1, further comprising separating said xylenes from said product stream.

7. The method of claim 1, wherein oxidizing comprises treating said stream with an oxidizing agent.

8. The method of claim 1, wherein said reacting step b comprises contacting said reaction mixture with a catalyst.

9. The method of claim 8, wherein said catalyst comprises niobic acid and its hydrates.

10. The method of claim 1, wherein the ratio of isobutyraldehyde to isobutanol in said first stream is about 1:1.

11. The method of claim 1, further comprising conducting said coupling step c in the presence of water.

12. The method of claim 1, further comprising conducting said coupling step c in the absence of water.

13. The method of claim 11, further comprising conducting said coupling step in the presence of an acid.

14. The method of claim 1, wherein said second stream further comprises one or more saturated or unsaturated mono- or polyhydroxylated octanes.

15. The method of claim 14, wherein said one or more octanes comprise 2,5-dimethylhex-4-en-3-ol and 2,5-dimethylhexane-2,4-diol.

16. The method of claim 14, further comprising dehydrating said one or more saturated or unsaturated mono- or polyhydroxylated octanes.

17. The method of claim 1, wherein said oxidizing comprises dehydrogenating.

* * * * *